(12) United States Patent
Craighead et al.

(10) Patent No.: US 7,267,797 B1
(45) Date of Patent: Sep. 11, 2007

(54) NANOFABRICATED PHOTON TUNNELING BASED SENSOR

(75) Inventors: Harold G. Craighead, Ithaca, NY (US); Jun Kameoka, Ithaca, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 897 days.

(21) Appl. No.: 10/010,939

(22) Filed: Nov. 7, 2001

Related U.S. Application Data

(60) Provisional application No. 60/248,287, filed on Nov. 14, 2000.

(51) Int. Cl.
- B32B 5/02 (2006.01)
- B32B 27/04 (2006.01)
- B32B 27/12 (2006.01)
- G01N 21/00 (2006.01)
- G01N 15/06 (2006.01)

(52) U.S. Cl. .............. 422/82.05; 422/50; 422/52; 422/55; 422/58; 422/68.1; 422/82.06; 422/82.07; 422/82.09; 422/82.11; 436/164; 436/172; 436/43; 436/63; 73/1.02; 977/920; 977/953; 977/957; 977/958; 977/834

(58) Field of Classification Search .............. 422/50, 422/52, 55, 58, 68.1, 82.05, 82.06, 82.07, 422/82.08, 82.09, 82.11; 436/164, 172, 63; 73/1.02; 977/920, 953, 957, 958, 834
See application file for complete search history.

(56) References Cited

U.S. PATENT DOCUMENTS

| | | | |
|---|---|---|---|
| 5,377,008 A * | 12/1994 | Ridgway et al. | 356/481 |
| 5,465,151 A * | 11/1995 | Wybourne et al. | 356/481 |
| 5,563,707 A * | 10/1996 | Prass et al. | 356/517 |
| 5,620,850 A * | 4/1997 | Bamdad et al. | 530/300 |
| 5,658,732 A * | 8/1997 | Ebersole et al. | 435/6 |
| 5,766,956 A * | 6/1998 | Groger et al. | 436/164 |
| 5,793,485 A * | 8/1998 | Gourley | 356/318 |
| 5,965,456 A * | 10/1999 | Malmqvist et al. | 436/514 |
| 6,331,438 B1 * | 12/2001 | Aylott et al. | 436/172 |
| 6,395,558 B1 * | 5/2002 | Duveneck et al. | 436/172 |
| 6,438,279 B1 * | 8/2002 | Craighead et al. | 385/12 |
| 6,493,090 B1 * | 12/2002 | Lading et al. | 356/484 |

OTHER PUBLICATIONS

Dähne, C., et al., "Detection of Antibody—Antigen Reactions at a Glass Liquid Interface: A Novel Fibre-Optic Sensor Concept", *Proceedings of the SPIE, vol. 514—2nd International Conference on Optical Fiber Sensors (OFS '84)*, (1984), 5-79.

* cited by examiner

*Primary Examiner*—Brian Sines
(74) *Attorney, Agent, or Firm*—Schwegman, Lundberg, Woessner & Kluth, P.A.

(57) ABSTRACT

A system and method for detecting changes in the refractive index of a fluid in a small test volume. A change in the refractive index can indicate a change in the chemical composition of the fluid. The test volume has a depth comparable to or less than the wavelength of incident light. In one embodiment, an internal surface of the volume is coated with a binding partner selected to bind with a targeted molecule. When the targeted molecule binds to the binding partner, the optical properties of the system change. The refractive index is determined by illuminating the test volume with laser light and measuring transmitted or reflected light.

12 Claims, 9 Drawing Sheets

US 7,267,797 B1

NANOFABRICATED PHOTON TUNNELING BASED SENSOR

RELATED APPLICATION

This application claims the benefit under 35 U.S.C. 119(e) of U.S. Provisional Application Ser. No. 60/248,287 filed Nov. 14, 2000, which is incorporated herein by reference.

GOVERNMENT FUNDING

The invention described herein was made with Government support by the Defense Advanced Research Projects Agency, through an Office of Naval Research grant number N00014-97-10-0779, and by the National Science Foundation, under contract number ECS-9876771. The United States Government has certain rights in the invention.

TECHNICAL FIELD OF THE INVENTION

The present invention relates generally to the field of chemical and biological sensors and, in particular, to a nanofabricated photon tunneling based sensor for detecting the presence of chemical or biological material.

BACKGROUND

Sensitive detection of the presence of a target substance is an important goal recognized by both science and industry. The target substance may be a chemical or biological entity. Often the target substance occurs in such small quantities that accurate detection is frustrated by the sensitivity limitations of the detector.

Surface plasmon resonance (SPR) biosensor systems have been developed which enable measurement of chemical and biological substances. Such devices operate on the principal that energy carried by waves of light photons can be transferred to electrons in a metal. The wavelength of light at which the energy transfer occurs is a function of the metal at the interface and the environment encompassing the metal. The maximum energy is transferred from the photons to the electrons at the resonance frequency, and thus, by monitoring the light reflected by the metal surface, it is possible to determine the resonant frequency. In particular, the light reflected by the metal surface is at a minimum at the resonant frequency. Typically, in SPR systems, the angle of minimum reflection is usually used as an indication of the plasmon resonance. At the interface of the metal and a dielectric, the electrons are excited which creates an electromagnetic wave extending a short distance above and below the interface. Consequently, a change in the environment at the interface is detectable as a change in the wavelength of the resonant frequency.

The principals of SPR are used for detecting the refractive index properties of a substance in one type of biosensor system. In particular, a change in the refractive index, caused, for example, by an antigen binding to an antibody, is manifested by a change in the resonant frequency.

In practice, however, SPR biosensors have limited utility. For example, the metal at the interface is often gold or silver, and thus, any elements that react with the metal may yield erroneous results. Also, the sensitivity of SPR biosensors is inadequate for some applications. In addition, the apparatus is often too large for practical field use. Typically, SPR biosensors require large samples, often measured in microliter or larger quantities.

A fibre-optic sensor is discussed in Dahne C. Sutherland R M, Place J F, Ringrose A S. "*Detection of antibody-antigen reactions at a glass-liquid interface: a novel fibre-optic sensor concept.*" Proceedings of Spie—the International Society for Optical Engineering, vol. 514, 1984, pp. 75-9 (hereinafter "Dahne"). Dahne discusses detecting in-line fluorescence resulting from evanescent waves internally guided through a waveguide. The waveguide, a standard PCS fiber with 0.6 micrometers core diameter, passes through a cylindrical flow cell in which the sample solution passes. Like SPR biosensors, Dahne appears to require a relatively large quantity of sample solution since the waveguide operates in a bath of the solution.

Other techniques of detecting the presence of a particular chemical composition have included staining or labeling. For example, genotyping efforts have included radioisotope labeling. Recognized disadvantages associated with the use of radioactivity include costs, hazards associated with radioactive materials, and undesirable delays associated with such techniques.

For the reasons stated above, and for other reasons stated below which will become apparent to those skilled in the art upon reading and understanding the present specification, there is a need in the art for a highly sensitive detection system and method that allows for detection of biological or chemical material.

SUMMARY

The above mentioned problems with detectors and other problems are addressed by the present invention and will be understood by reading and studying the following specification. A system and method are described for detecting changes in the index of refraction of an extremely small quantity of fluid.

By way of overview, the system includes a fluid channel, or duct, adapted to receive a small volume of sample fluid via an opening to the interior of the channel. The duct is fabricated of optically transparent material arranged in a sandwich, or laminate, structure using nanofabrication or micromachining technology. The system may be illuminated with a collimated light directed at a transparent, or translucent, surface of the channel. As used herein, the optical quality of translucency falls on a continuum between opaque and transparent as it relates to the transmission of visible light. Thus, a transparent structure allows transmission of most light, a translucent structure allows transmission of some light, and an opaque structure prevents transmission of most, or all, light. Light falling on the channel is reflected, or transmitted, based on the optical properties of the contents of the channel. The refractive index of fluid in the channel is thus detectable by measurement of light emerging from the channel. Reflected light or transmitted light may be measured.

The absolute index of refraction can be determined using the present system. In addition, a differential index of refraction, based on a comparison of sample substances, can be determined using the present system. In one version, the interior surface of the channel includes an immobilized binding partner which couples to a predetermined analyte in a lock and key fashion. The refractive index of the system with an analyte bound to a binding partner is thus detectable. The nanometer dimensions of the channel accentuate the surface effects of the fluid.

In a system having a binding partner immobilized on the interior of the channel, a baseline index of refraction of the channel is determined. The baseline index of refraction is then compared with the index of refraction of the channel after exposure to the sample substance and an opportunity for the binding partner to bind to the sample solution. The baseline index of refraction may be prepared using a bulk solution introduced through the opening or it may be determined without the bulk solution.

DETAILED DESCRIPTION

The following detailed description refers to the accompanying drawings which form a part of the specification. The drawings show, and the detailed description describes, by way of illustration specific illustrative embodiments in which the invention may be practiced. These embodiments are described in sufficient detail to enable those skilled in the art to practice the invention. Other embodiments may be used and logical, mechanical, electrical and chemical changes may be made without departing from the scope of the present invention. The following detailed description is, therefore, not to be taken in a limiting sense.

The detector described herein is sensitive to the index of refraction of a sample substance. Determination of the index of refraction of a chemical or biological sample can be helpful in detecting or identifying the presence of a target substance in the sample.

Figure 1:
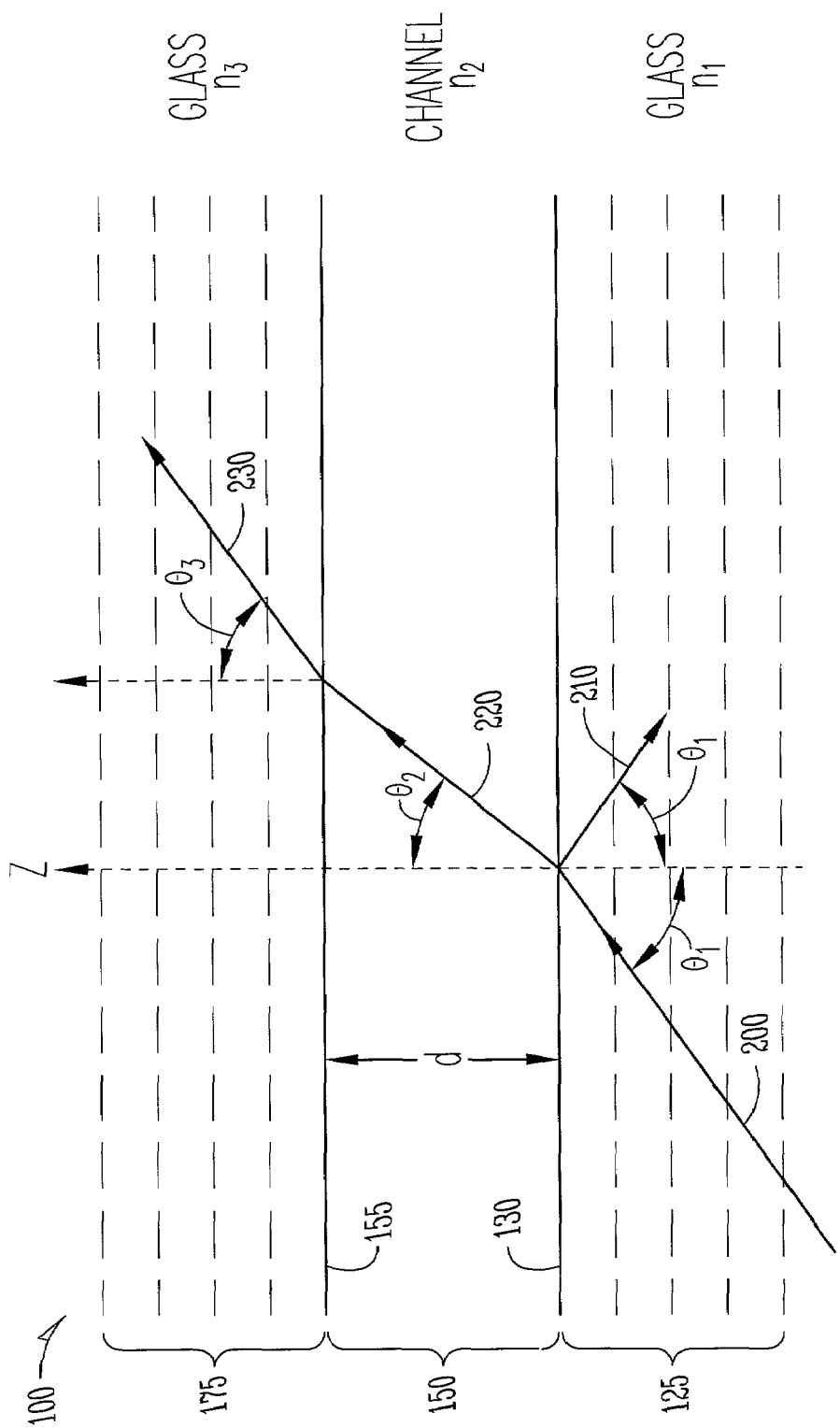
FIG. 1 illustrates light rays directed through a three element optical system according to an embodiment of the present subject matter.

FIG. 1 illustrates the optical principals underlying the measurement and determination of the index of refraction for a three element system when viewed on edge. The three elements have index of refractions denoted as $n_1$, $n_2$ and $n_3$ with $n_1$ different from $n_2$ and $n_2$ different from $n_3$. Incident light ray 200 is shown in the figure as traveling through the first element, herein denoted as plate 125, having refractive index $n_1$, at incident angle $\theta_1$ measured relative to vertical axis Z. With a sufficiently low incident angle $\theta_1$, light ray 200 is both refracted and reflected upon entry into medium 150 at interface 130. Interface 130 represents the boundary between plate 125 and the second element, medium 150. Refracted light ray 220 traverses medium 150 at refraction angle $\theta_2$. Reflected light ray 210 passes through plate 125 at reflection angle $\theta_1$. Refracted light ray 220 travels through thickness d of medium 150, having refractive index $n_2$ and impinges on interface 155. Interface 155 represents the boundary between medium 150 and the third element, plate 175. At interface 155, the incident light, herein shown as a refracted light ray 220, is further refracted at angle $\theta_3$ according to refractive index $n_3$ of plate 175.

Reflected and refracted light rays emerge from the illustrated system as determined by the refractive indices $n_1$, $n_2$, $n_3$, dimension d, the wavelength of incident light ray 200 and angle $\theta_1$. Light ray 230 corresponds to light transmitted through the system. Light ray 210 corresponds to light reflected by the system. In one embodiment, plate 125 and plate 175 are both glass and have $n_1=n_3$ although the present subject matter is not so limited.

Figure 2:
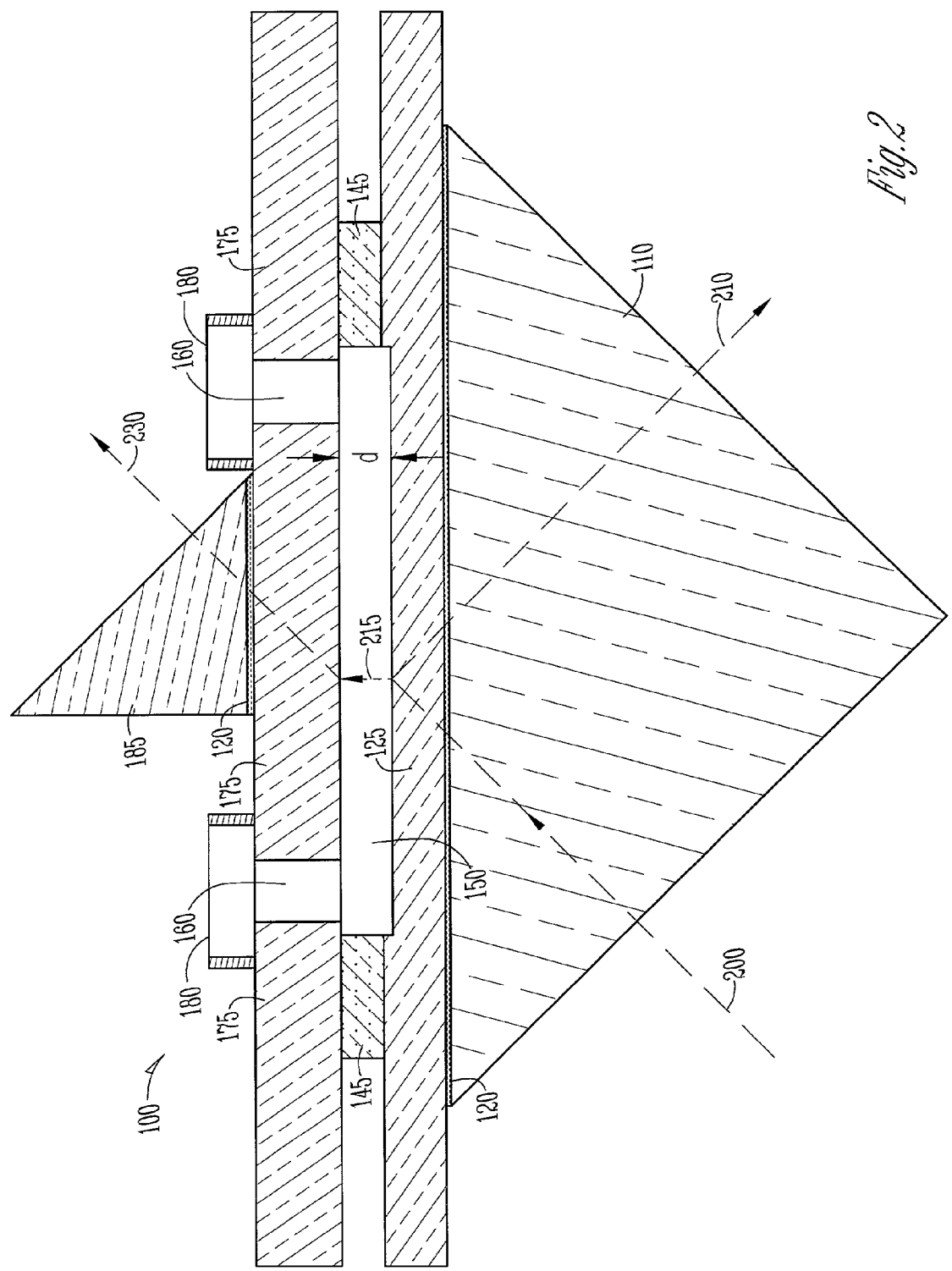
FIG. 2 illustrates a cross sectional view of an embodiment of the present system.

FIG. 2 illustrates a cross-sectional view of detector 100 according to the present system. Detector 100 includes a laminated structure having an upper plate 175. Plate 175 is optically transparent and may be fabricated of glass. Plate 175 may have a first and second hole, or port, each labeled 160. A first and second reservoir 180 is bonded atop each of first and second port 160. Reservoir 180 may be a tubular segment of aluminum. Anodically bonded to the lower surface of plate 175 is a layer of amorphous silicon 145. Amorphous silicon 145, and plate 125, are etched to define the walls of channel 150. The bond between the walls and plate 125 can be viewed as a sealed joint, thus preventing fluid migration. The channel volume is in the range of 10 to 100 nl, with a typical volume for one embodiment of 16 nl. The width and length dimensions of channel 150 are sufficiently small, with typical dimensions of 2 mm and 4 mm, respectively. Amorphous silicon 145 is also bonded to lower plate 125. Lower plate 125 is optically transparent and may be fabricated of glass. The indices of refraction of plate 125, channel 150, and plate 175 are $n_1$, $n_2$, $n_3$, respectively.

The optical paths of ray 200, ray 230, and ray 210 are represented in a simplified manner to more clearly illustrate the structural configuration of detector 100. It will be appreciated that light transitioning between surfaces having different indices of refraction will be both reflected and refracted, and therefore, at each interface, multiple rays may be present. The multiple rays are not illustrated in FIG. 2 for the sake of clarity.

Light ray 200 is transmitted through coupling prism 110, index matching oil 120 and plate 125. Coupling prism 110 may be fabricated of BK 7 glass. BK 7 glass is recognized for efficiently transmitting light throughout the near-ultraviolet, visible and near-infrared spectra. Index matching oil 120 can reduce Fresnel reflection losses, minimize etaloning problems and improve transmission wavefront quality. Etaloning is an instrumental artifact which reduces accuracy.

In FIG. 2, incident light ray 200 reflects at the interface of channel 150 and plate 125, as shown by ray 210. Ray 210 is transmitted through plate 125, index matching oil 120 and prism 110.

In addition to reflected ray 210, incident light ray 200 is refracted at the interface of channel 150 and plate 125, as shown by ray 215. Ray 215 is transmitted through channel 150, and the contents of channel 150. At the interface of channel 150 and plate 175, light ray 215 is refracted and transmitted through plate 175, index matching oil 120, and emerges from detector 100 at prism 185. Coupling prism 185 may be fabricated of BK 7 glass.

Coupling prisms 110 and 185 may be of the same or different material. Also, the matching oil 120 at prism 110 and prism 185 may be the same or different.

Figure 3:
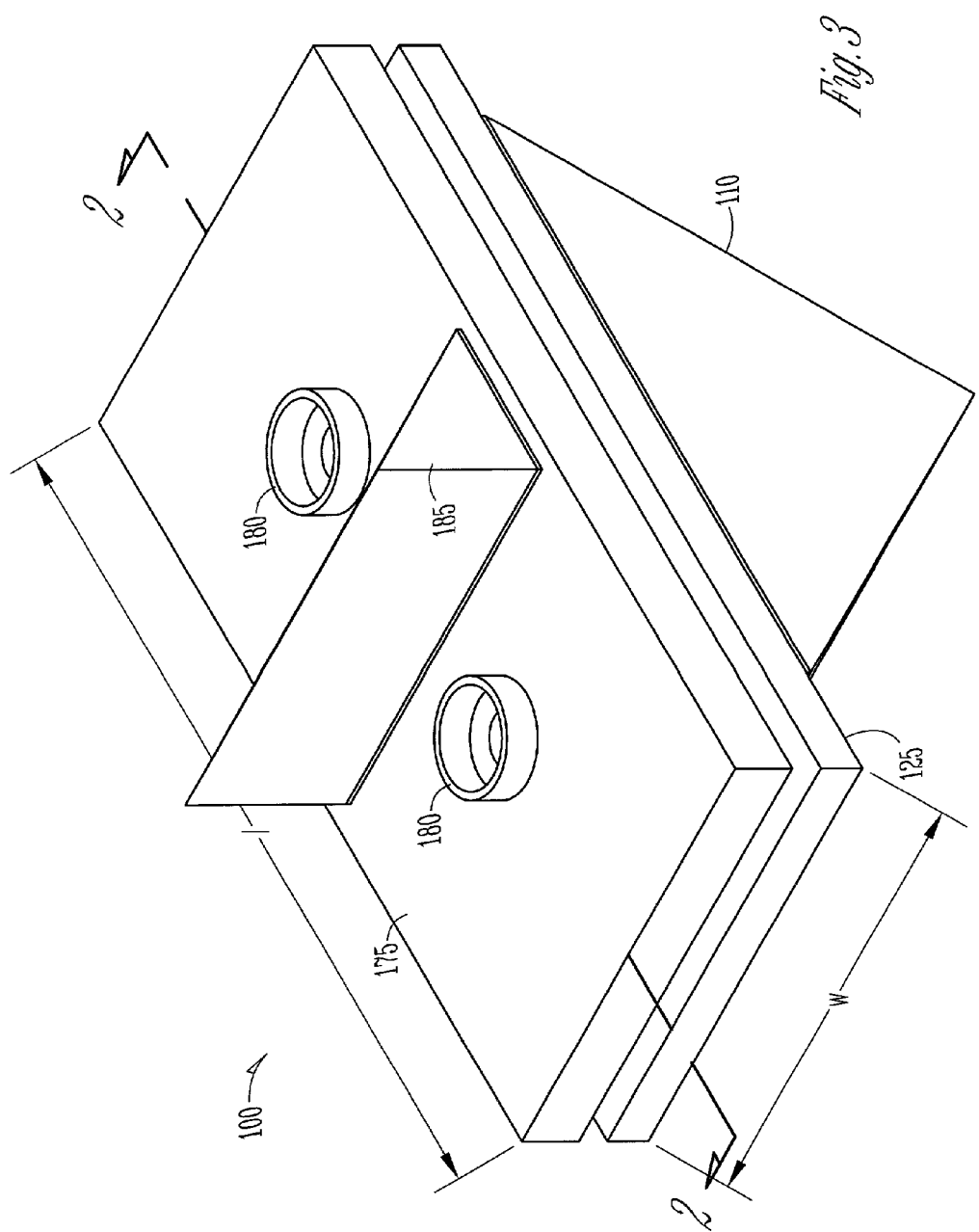
FIG. 3 illustrates an isometric view of one embodiment.

FIG. 3 illustrates an isometric view of one embodiment of detector 100 according to the present system. Detector 100 has length, denoted herein as I, and width, denoted herein as w. In one embodiment, the length is 2 cm and the width is 1.5 cm. Other length and width dimensions are also contemplated. The figure also illustrates reservoirs 180, plate 175, plate 125, prism 185 and prism 110. Amorphous silicon 145 is not visible in the figure. Cut line A-A corresponds to the view illustrated in FIG. 2.

Figure 4:
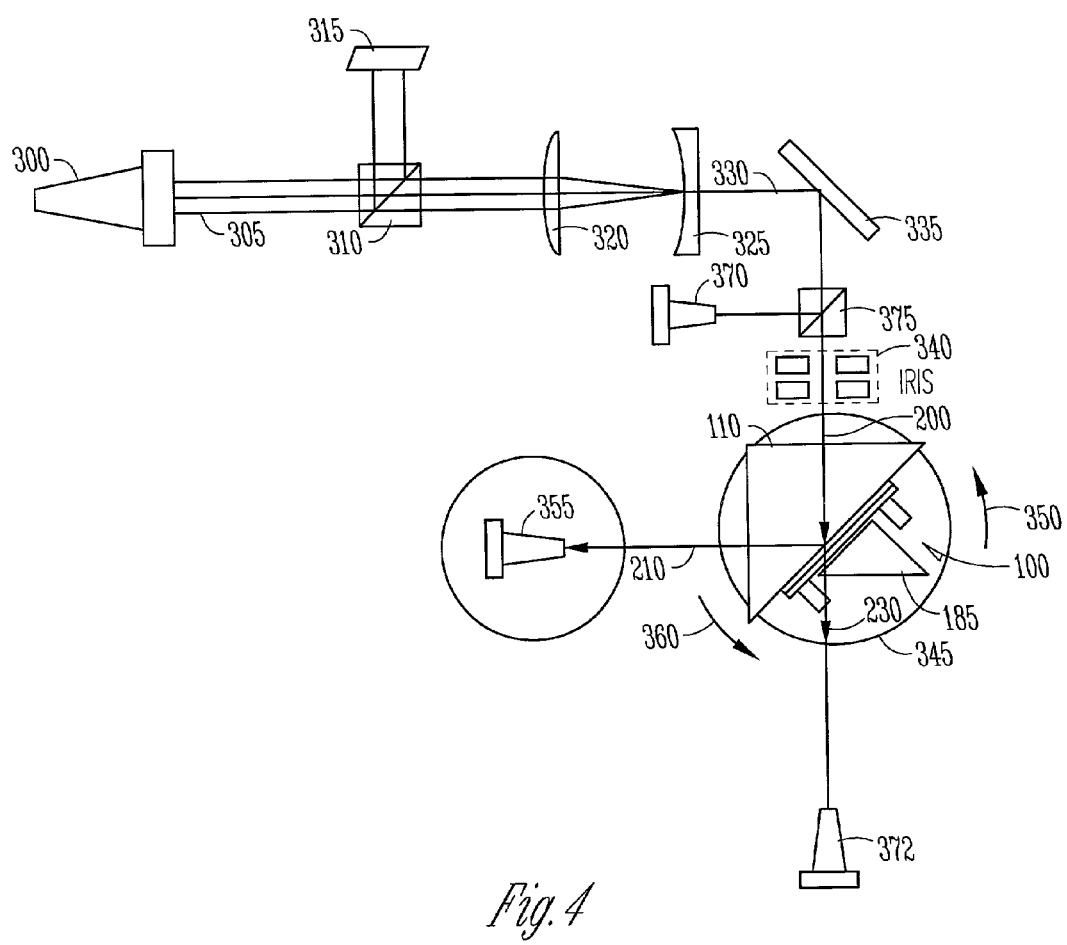
FIG. 4 graphically illustrates optical apparatus for determining an index of refraction according to the present subject matter.

FIG. 4 illustrates one version of an optical configuration suitable for determining the index of refraction using detector 100. Light source 300 is a laser beam that projects light beam 305 at polarizing beam splitter 310. In one embodiment, light source 300 is a diode laser having a wavelength of 670 nm. Preferably, light source 300 emits collimated light. Preferably, thickness d of channel 150, as shown in FIGS. 1 and 2, is comparable to or less than the wavelength of light source 300, however, d may be greater than the wavelength of light source 300. Polarizing beam splitter 310 transmits light of one polarization and reflects light of the orthogonal polarization. In the configuration shown in the figure, splitter 310 transmits a p-wave beam and reflects all other light at beam dump 315. Preferably, beam dump 315 is capable of dissipating the power of the laser without significant reflection or heating. The resulting p-wave beam is then transmitted to convex lens 320, followed by concave lens 325. In one embodiment, convex lens 320 has a focal length of 145 mm and concave lens 325 has focal length of 25 mm. Other focal lengths, and lens configurations are also contemplated. Convex lens 320 and concave lens 325 serve to reduce the light beam, herein denoted as 330, to a spot having an approximate diameter of 1 mm. Preferably the spot diameter is less than the width of channel 150 of detector 100. Light beam 330 is reflected by mirror 335 and is further processed by polarizing beam splitter 375 and a first portion is directed to power meter 370 and a second portion is gated through iris 340, thus forming incident light ray 200. Detector 100 is affixed to precision rotational stage 345, having angular resolution of approximately 0.16 degrees. As previously described, ray 200 enters detector 100 via prism 110. Light reflected by detector 100 emerges as ray 210. Ray 210 is received by powermeter 355. Transmitted light ray 230 may also be received and measured by powermeter 372.

In operation, precision rotational stage 345 is rotated in the direction shown by arrow 350 to increase the angle of incidence $\theta_1$ of ray 200. Powermeter 355, or powermeter 372, are positioned, as indicated by arrow 360, to maintain alignment with the reflected ray 210, or transmitted ray 230, respectively. In particular situations, it may be desirable to measure one, or the other, or both of ray 230 and ray 210, in order to achieve certain advantages.

At a sufficiently high angle of incidence $\theta_1$, light illuminating channel 150 is totally internally reflected, light ray 210 reaches a maximum intensity and light ray 230 reaches a minimum intensity. Such an angle is referred to as the critical angle of incidence and provides a measure of the index of refraction for the system, including channel 150, as a function of angle of incidence. The critical angle of incidence, and thus, the refractive index may be determined by various means. For example, FIG. 4 illustrates a system providing relative movement between detector 100 and the incident light by means of rotational stage 345. Other means of determining the critical angle are also comprehended. For example, the critical angle may be determined by an array of light sources, with each light source directed at channel 150. The critical angle may also be determined by a single light source and a repositionable mirror that casts a light ray having a varying angle of incidence on channel 150.

Figure 5:
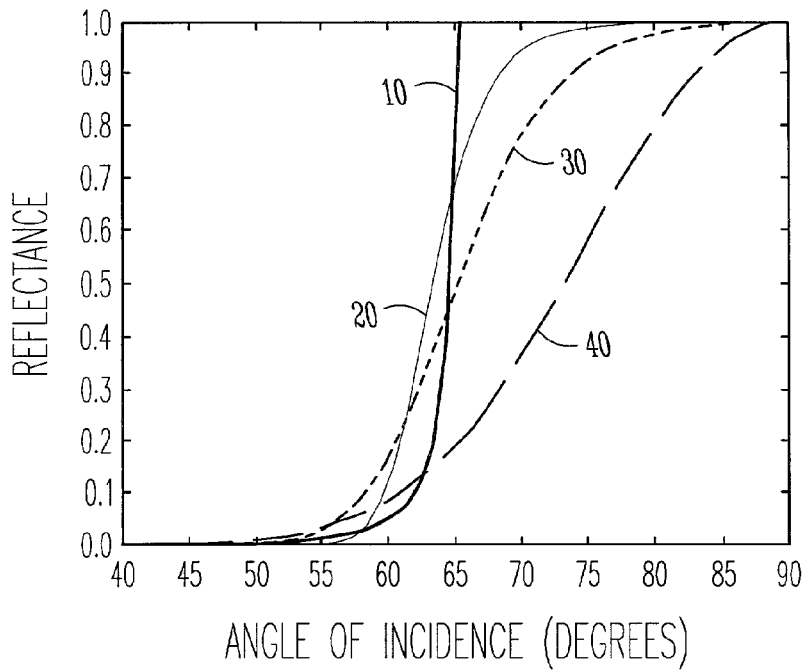
FIG. 5 graphically illustrates reflectance as a function of angle of incidence for selected gap, or thickness, dimensions.

FIG. 5 graphically illustrates reflectance as a function of angle of incidence for selected gap, or thickness, dimensions. The figure illustrates reflectance for incident light having a free-space wavelength of 670 nm, using a detector 100 having plate 125 and plate 175 both made of glass having a refractive index of 1.47 and with water in channel 150. In the figure, curve 10 represents a dimension d of infinity. Curve 20 shows dimension d of 600 nm, curve 30 shows dimension d of 400 nm and curve 40 shows dimension d of 200 nm. With reduced dimension d, light more readily tunnels across the gap from plate 125 to plate 175.

Figure 6:
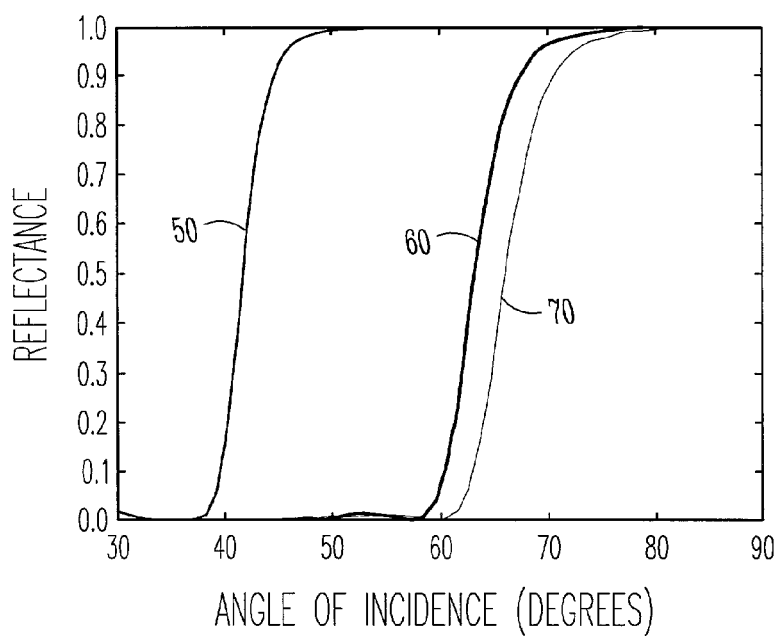
FIG. 6 graphically illustrates the effect of refractive index of a fluid in a channel.

FIG. 6 graphically illustrates the effect of refractive index of a fluid in channel 150. In the figure, dimension d of detector 100 is 600 nm. Curve 50 illustrates a fluid having a refractive index of 1.000. Curve 60 and 70 illustrate fluids having a refractive index of 1.332 and 1.36, respectively. The figure graphically demonstrates the strong relationship between reflectance and the index of refraction of material in channel 150.

Fabrication of Photon Chip Detector

Figure 7A:
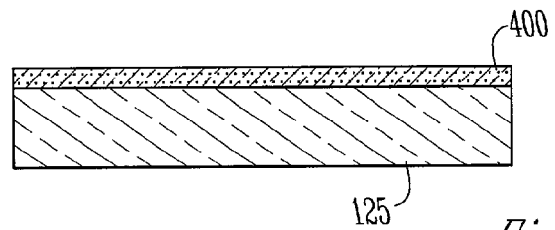
FIGS. 7A, 7B, 7C and 7D illustrate a method of fabricating an element of one embodiment of the present system.

Detector 100 may be fabricated using any of a number of semiconductor fabrication techniques. An exemplary fabrication process is illustrated in FIGS. 7A, 7B, 7C and 7D, and is described as follows:

FIG. 7A illustrates one embodiment wherein detector 100 is fabricated using a first substrate of wafer glass, such as silicon wafer constraint substrate glass offered by Corning. Examples of wafer glass include Corning Pyrex® Borosilicate glass code 7740 and Lithia Potash Borosilicate glass code 7070, both known for exhibiting good thermal expansion match with silicon, and both of which may be anodically bonded to silicon. Common names for such glass include borosilicate, low expansion or Type I glass. Standards describing Type I, Class A borosilicate glass includes federal specification DD-G-541b and ASTM E-438, or U.S. Pharmacopoeia specs for Type I Borosilicate Glass. Corning 7740 has a refractive index of 1.470 which is greater than that of the sample substance. The first substrate, referred to in the figures as plate 125, may be fabricated of other materials exhibiting optical transparency and conducive to photolithography, nanofabrication, or micromachining technologies.

In one embodiment, a layer 400 is deposited onto the substrate to facilitate bonding of a second substrate, referred to as plate 175. Layer 400 may be of amorphous silicon or other such layer. Layer 400 may be deposited using low pressure chemical vapor deposition ("LPCVD") or plasma enhanced low pressure chemical vapor deposition ("PECVD"). The thickness, or depth, of layer 400 may be in the range of 50 to 300 nm, with a typical dimension of 80 nm.

Figure 7B:
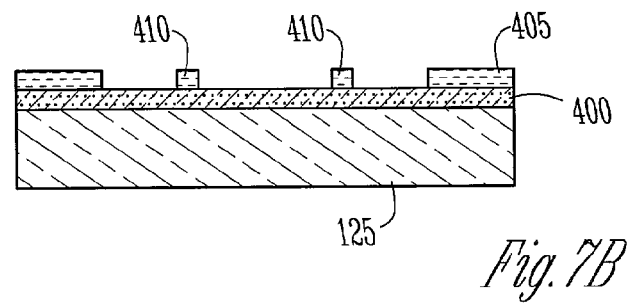
Figure 7C:
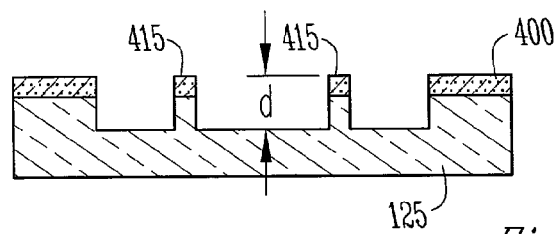

Photolithography processes are used in a subsequent step to deposit photoresist 405 to define channel 150, as in FIG. 7B. Photoresist 405 may be Shipley 1805 or other comparable product. Channel 150 is etched into layer 400 and substrate 125 in a reactive ion etch ("RIE") chamber using carbon tetrafluoride ("$CF_4$"), or other suitable etchant, as shown in FIG. 7C. The depth of the etching defines the depth d of channel 150. In one embodiment, the channel is etched to a depth in the range of 150 to 700 nm, with typical dimensions of approximately 300 nm or 630 nm. In the event that the first substrate is fabricated using bulk processing, then individual plate 125 may then be cut out as a single chip and each chip can be anodically bonded to the second substrate, plate 175, as in FIG. 7D.

In different embodiments, plate 175 includes one or two holes 160. In an embodiment with a single hole 160, alternative means of venting channel 150 are provided. One such means includes providing a gap in the channel wall 145 that vents to the exterior. The hole is fitted with a reservoir 180 to enable a human operator to inject the sample substance into channel 150. In the figures, reservoir 180 is illustrated as a short section of aluminum tubing bonded to the upper plate 175. Other means of providing reservoir 180, or means of interfacing with an operator, are also contemplated, including a miniature manifold.

Figure 7D:
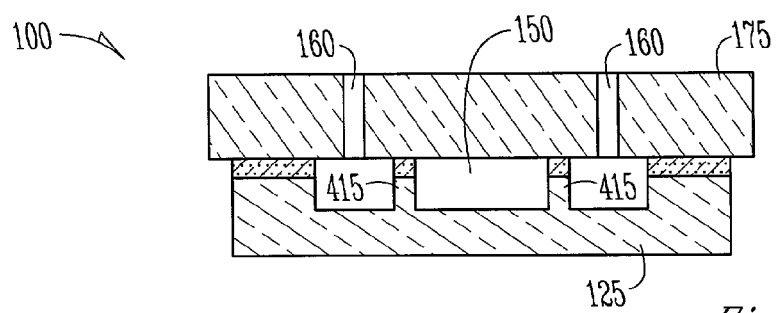

In one embodiment, channel 150 includes one or more support pillars 415. Pillar 415 provides structural strength and serves to maintain channel dimension d between plate 125 and plate 175. FIG. 5B illustrates two pillar photoresist regions 410 defined by photoresist 405 atop layer 400. In FIG. 7C, pillars 415 are etched to depth d. In FIG. 7D, pillars 415 appear within the interior of channel 150 and support plate 175 by exerting force on plate 125.

Example Application

The following describes a particular embodiment of the present subject matter when used to detect the presence of ethanol. Detector 100 was fabricated as described above with channel 150 having a thickness, dimension d, of approximately 686 nm, length of 4 mm and width of 2 mm, thus yielding a fluid capacity of 16 nl.

The sample fluid was injected into reservoir 180 and allowed to migrate into channel 150 by capillary forces. An optical configuration, as described relative to FIG. 4 above, was used to detect the presence of ethanol in water. Precision rotational stage 345 was operated, while monitoring ray 210 with powermeter 355, to determine the reflectivity of the system as a function of angle of incidence of ray 200.

Detector 100 was rinsed between sample fluids by injecting water and allowing capillary action to draw fluid through channel 150. Detector 100 was dried by heating.

A series of experiments, each including rinsing, heating and injection of sample fluid was performed using water, water with 1% ethanol and water with 10% ethanol.

Figure 8:
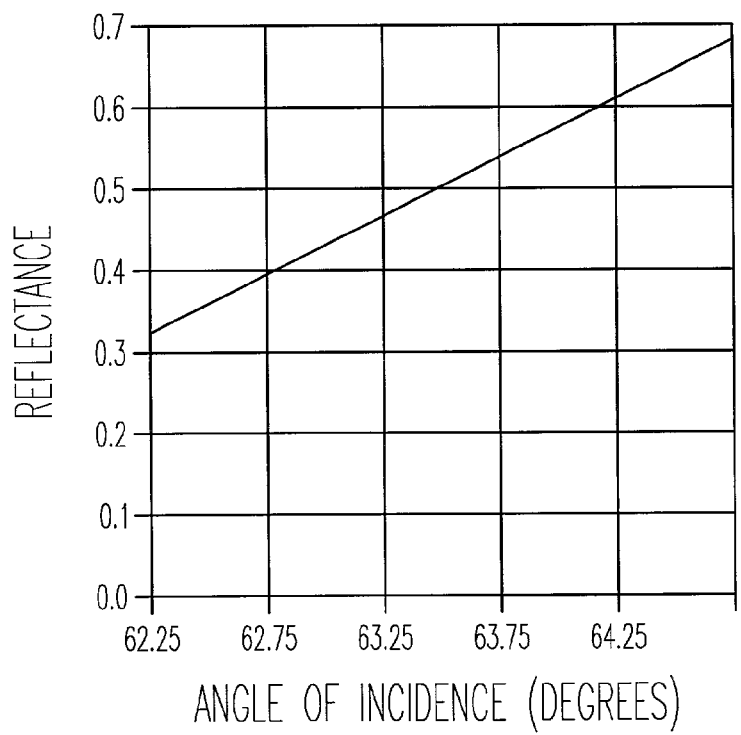
FIG. 8 graphically illustrates performance of one embodiment of the present system when exposed to water.

FIG. 8 graphically illustrates some of the results with reflectance represented on the ordinate and angle of incidence on the abscissa. FIG. 8 illustrates detector 100 with water in channel 150. Detector 100 has a channel thickness of 686 nm and the wavelength of the light generated by light source 300 is 670 nm. In FIG. 8, data is shown for incidence angles between 62.25 and 64.5° using a step size of 0.16°. In one embodiment, it was determined that the critical angle for water is 64.97°.

Detector 100 provides information concerning light intensity as a function of the angle of incidence. For example, the relative difference between the intensity of refracted light among three sample fluids provides information concerning the identity, or composition, of the three sample fluids.

Figure 9:
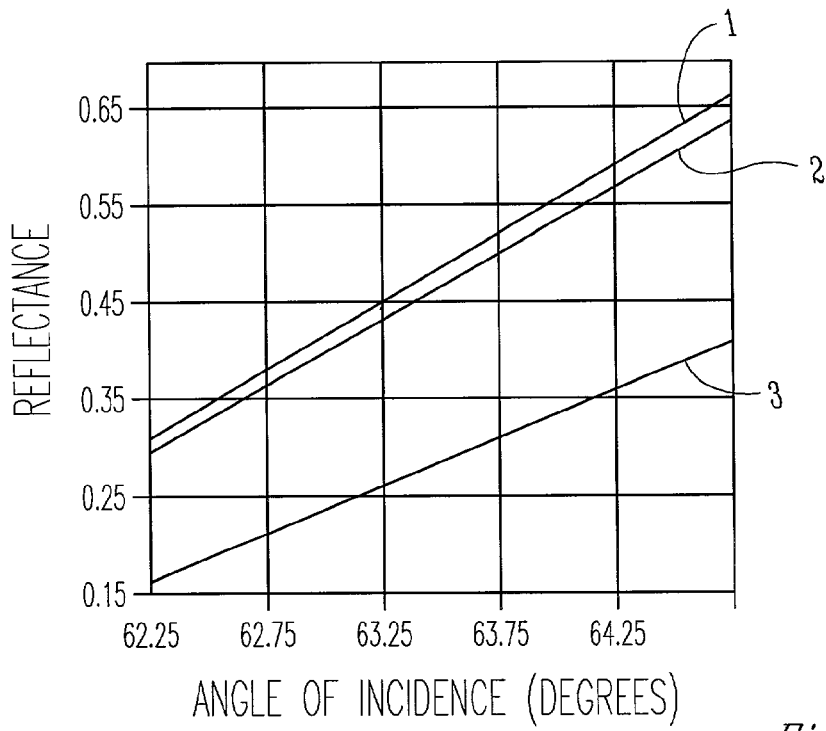
FIG. 9 graphically illustrates performance of one embodiment of the present system when exposed to water, and water with ethanol.

Detector 100 was further tested using sample fluids with water and a solution of 10% ethanol and water and a solution of 1% ethanol and the results are illustrated in FIG. 9. FIG. 9 illustrates reflectance as a function of the angle of incidence, wherein curve 1 represents water, curve 2 represents water with 1% ethanol and curve 3 represents water with 10% ethanol.

On the basis of the foregoing data, it has been determined that a measurable refractive index change can be calculated in the range of between 0.00034 to 0.00038. Refractive index changes of greater or less than this range can also be measured using the disclosed subject matter.

Figure 10:
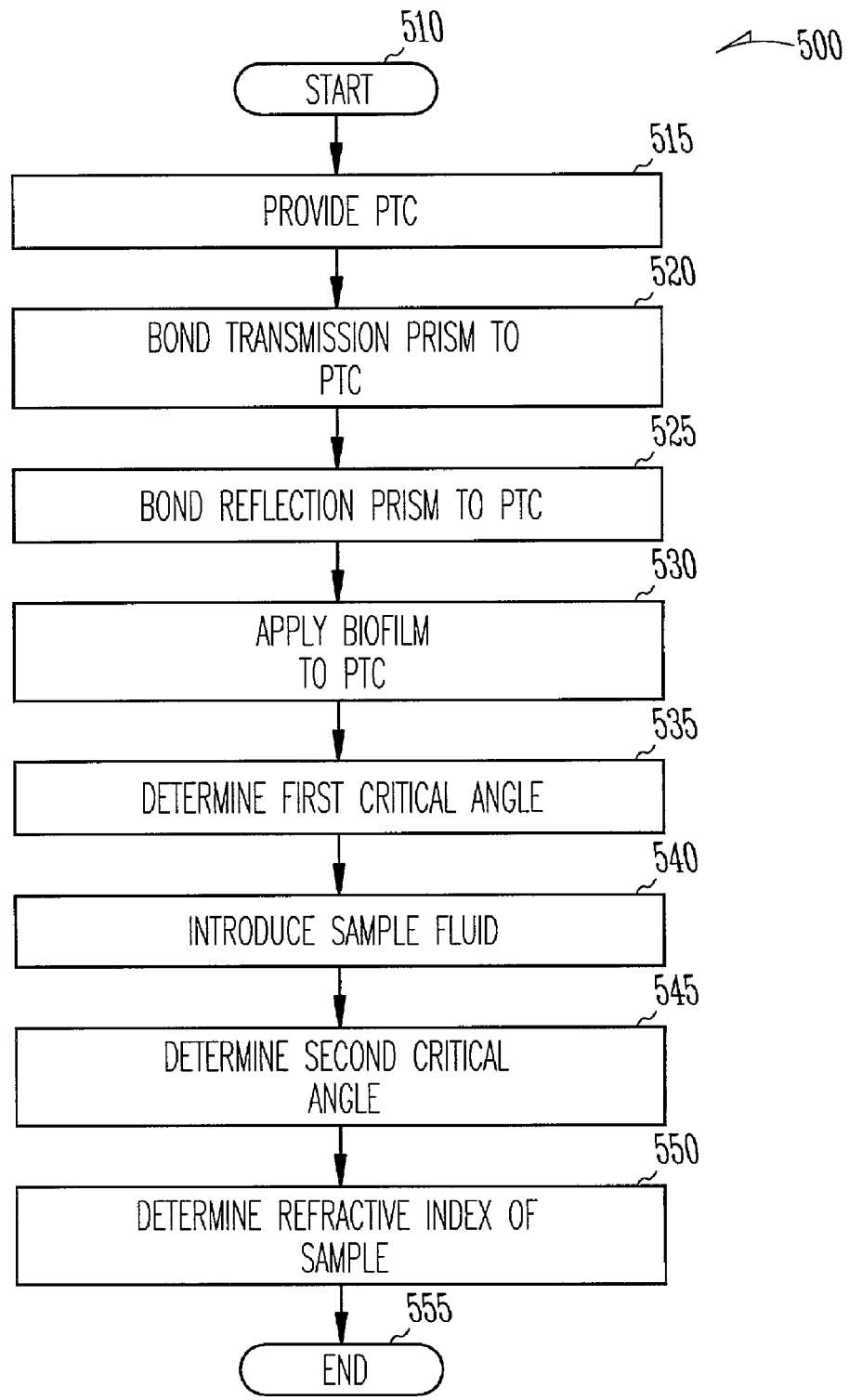
FIG. 10 illustrates a flow chart of a method for detecting the presence of a target substance in a particular sample fluid, pursuant to the present system.

FIG. 10 illustrates a flow chart of method 500 for detecting the presence of a target substance in a particular sample fluid, pursuant to the present system. Beginning at 510, it is assumed that optical light source and powermeter apparatus are available. At 515, the photon tunnel chip (PTC) or detector 100, is provided. The dimensional parameters of detector 100 are selected according to such factors as the physical and chemical properties of the target substance and the wavelength of the light source. At 520, prism 185 is coupled to detector 100 using suitable index matching oil. At 525, prism 110 is coupled to detector 100 using suitable index matching oil. At 530, a biofilm is immobilized to the interior of channel 150. The biofilm may be introduced by injection into the reservoir and capillary action into channel 150. In one embodiment, the biofilm is permanently affixed to the interior of channel 150. Alternatively, the biofilm can be removed and replaced using suitable procedures. At 535, the optical light source and powermeter, of which FIG. 4 illustrates one embodiment, are manipulated to determine the critical angle of incidence for detector 100 having a biofilm bonded to the interior of channel 150. At 540, the sample fluid suspected of containing the target substance is introduced into channel 150. At 545, the critical angle of incidence is determined with the sample fluid in channel 150. At 550, analytical techniques are applied to determine the differential refractive index to determine if the target substance is present. The method ends at 555.

ALTERNATIVE EMBODIMENTS

Figure 11A:
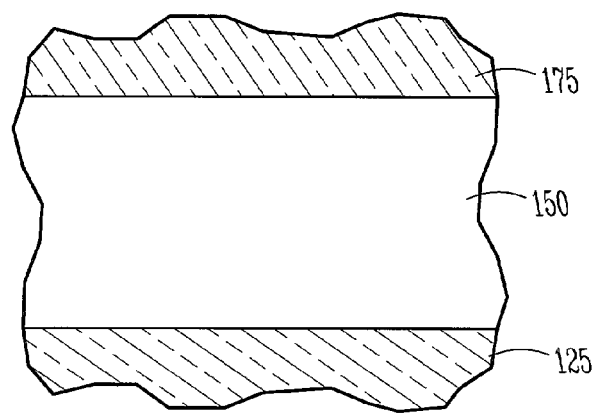
FIGS. 11A, 11B and 11C illustrate apparatus for use with a method of detecting a target substance using a biofilm.
Figure 11B:
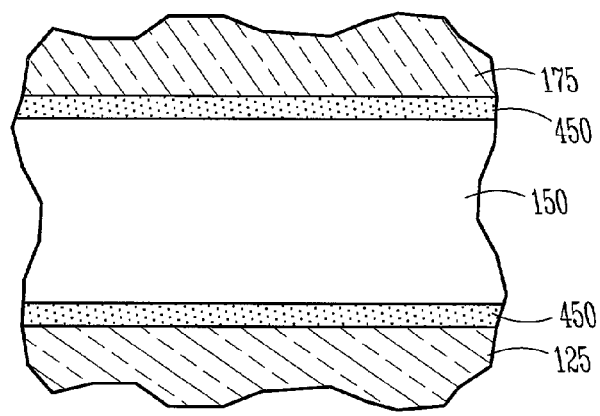
Figure 11C:
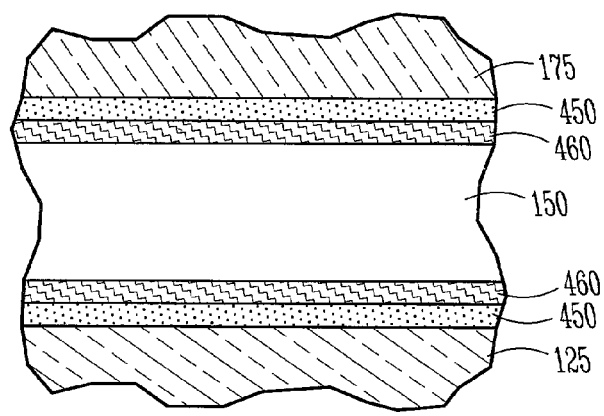

The principals of the present subject matter allow numerous variations tailored to the needs of a specific application. For example, detector 100 may be adapted to detect the presence of a target chemical or biological substance. In one embodiment, detector 100 includes an immobilized binding partner on an interior surface of channel 150. The immobilized binding partner, or biofilm is selected to bind with a particular substance in a "lock and key" fashion. FIGS. 11A, 11B and 11C are illustrative with each figure depicting a portion of channel 150 including plate 125, plate 175 and channel 150. In FIG. 11A, the contents of channel 150 are in contact with the plate 125 and plate 175. The refractive index of sample fluid in channel 150 can be determined as described above. In FIG. 11B, the interior surfaces of channel 150 are coated with biofilm 450. Biofilm 450 may be installed in channel 150 by means of capillary action in a manner akin to the installation of the sample fluid. Biofilm 450 binds with a particular target substance. In FIG. 11C, sample fluid including particular target substance 460 is shown to have bonded with biofilm 450. Target substance 460 may be introduced into channel 150 by means of capillary action. Target substance 460 binds to biofilm 450 and alters the index of refraction of channel 150.

The altered refractive index is thus detectable. In various embodiments, biofilm 450 may bind with one or more targeted substances.

Biofilm 450, comprising one or more binding partners, is selected to bind to a desired target substance, or substances, wherein said bound target substance, or substances, is then detected by detector 100. For example, one protein (such as an antibody) may be used as a binding partner for purposes of detecting a second protein (such as an antigen). By way of example only, and not by way of limitation, other pairs include using a receptor for detecting a ligand such as using a cellular receptor to detect a ligand that binds to such receptor, using a protein for detecting a peptide, using a protein for detecting a DNA, using a first DNA sequence to detect a second DNA sequence, using a metallic ion to detect a chelator, and using an antibody, or an antibody fragment, for detecting an antigen or analyte. It will be recognized that the aforementioned examples bind to each other in a "lock and key" fashion by ionic bonding, covalent bonding or a combination thereof. In some cases, the binding partner may bind specifically to a single target substance or subunit thereof. Consequently, either the "lock" can be immobilized in channel 150 for detecting the "key" or the "key" can be immobilized in channel 150 for detecting the "lock." As an example, a peptide may be the binding partner in channel 150 for use in detecting a protein. The binding partner immobilized in channel 150 can be DNA and thus, the present system is responsive to the substantial DNA complement. The bound, or "hybridized" DNA sequences can then be treated or "washed" under various conditions of stringency so that only DNA sequences that are highly complementary (e.g., that has high sequence identity) will be retained in channel 150.

The binding partner can also bind to a plurality of substances, in which case, detector 100 will indicate detection of any substance binding to channel 150. In addition, more than one binding partner may be immobilized in a particular channel 150 to enable detection of multiple molecules. Multiple binding partners may be immobilized in the same or different regions of channel 150.

The binding partner can include an antibody for detection of an antigen, or binding partner includes an antigen for detection of an antibody. Examples of antigens include proteins, oligopeptides, polypeptides, viruses and bacteria. For instance, antigens include $OMP_a$, $OMP_b$ and $OMP_c$, commonly referred to as outer membrane protein "a" "b" and "c." In such cases involving antigens, the interaction includes one or more amino acid interactions wherein the amino acids are spatially arranged to form two complementary surfaces in three dimensions. Each surface includes one or more amino acid side chains or backbones.

The binding partner can include an antibody for detection of a hapten, or the binding partner can include a hapten for detection of an antibody. Haptens tend to be much smaller than antigens and include such compounds as transition metal chelators, multi-ring phenols, lipids and phospholipids. In such cases involving haptens, the interaction includes an intermolecular reaction of a surface of the hapten with one or more amino acids of the antibody, wherein the amino acids of the antibody are spatially arranged to form a complementary surface to that of the hapten.

The interaction between amino acids, such as antibody-antigen or antibody-hapten, arises by van der Waal forces, Lennard-Jones forces, electrostatic forces or hydrogen bonding. Consequently, immobilized binding partner interacts with the targeted substance in a manner beyond that of simple absorption of analyte into a matrix of some type. The interaction of binding partner with the target substance is characterized by rapid bonding, preferably bonding that is not reversible under ambient conditions, thus reducing the time required for reliable detection using detector 100.

Hybrid antibodies are also contemplated for either the target substance or binding partner. For example, a portion of a first antibody may be cleaved and a second antibody may be bonded to the remaining portion of the first antibody, thus forming a hybridized antibody. Such an antibody may subsequently bind with two forms of antigens or haptens. As yet another example, a third antibody may be bonded to the remaining portion of the first antibody, thus enabling subsequent bonding to additional antigens or haptens. The use of hybridized antibodies in detector 100 yields a detector sensitive to multiple substances and may be desirable for certain applications where detection of two or more analytes is desired.

Binding partner is affixed, or immobilized, to channel 150 using any of a number of techniques, including absorption, covalent bonding with or without linker or spacer molecules or complexation.

A system including a plurality of discrete detectors 100 may be assembled in an array. Each detector 100 in an array may have a unique biofilm 450 immobilized on the interior of each channel 150. Such a configuration may be beneficial for detecting the presence of multiple target substances using a single device or system. Alternatively, more than one detector 100 may have the same biofilm 450. Such an array may be beneficial for purposes of assuring accuracy and providing redundancy. Also, each detector 100 in an array may have the same physical dimensions or each detector 100 may have different dimensions. The dimensions of each detector 100 may be tailored to meet particular detection needs. Parameters, or dimensions, that may be tailored include, but are not limited to, channel dimensions and wavelength of source lighting.

A system may include integrated optical sensors coupled to detector 100. A system may also include integrated waveguides. For example, a microfluidic channel, or detector 100, may be located along the length of a light waveguide. Miniaturized rotational stages or other means of determining the critical angle may also be included. It is contemplated that a self-contained unit of under 5 cm square can be fabricated for detection of a plurality of target substances.

Plate 125 and plate 175 of detector 100 may both be optically translucent. In such a case, either, or both, of the reflected and transmitted light rays may be measured. Alternatively, one plate may be translucent and the other plate may be opaque, in which case, the incident light would fall on the translucent plate and the reflected light would be monitored.

Structural variations are also contemplated. For example, the introduction of the sample fluid to channel 150 may be by any suitable means. Hole 160 and reservoir 180 are illustrated in the figures relative to plate 175, however, plate 125 may also be used. In addition, channel 150 may include one or more support pillars. In one embodiment, a plurality of pillars, each having a diameter of 5 µm, are positioned with center to center distance of 100 µm. Other dimensions and spacings are also contemplated. Also, structural support may be provided in the region of the channel 150 below reservoir 180. For example, multiple linear support elements may be included to bear the weight of reservoir 180. Such support elements are tailored to provide mechanical strength without interfering with the optical measurement of the index of refraction of channel 150. Structural support elements and pillars may be positioned on the interior of channel 150.

CONCLUSION

Although specific embodiments have been illustrated and described herein, it will be appreciated by those of ordinary skill in the art that any arrangement which is calculated to achieve the same purpose may be substituted for the specific embodiment shown. This application is intended to cover any adaptations or variations of the present invention.

The invention claimed is:

1. A refractive index detector comprising:
a duct, said duct having an interior surface and a substantially parallel gap formed by a first wall and a second wall of said duct, said first wall and said second wall are transparent, said duct configured to receive a solution and configured to reflectively communicate light to an optical sensor as a function of said solution in said duct and as a function of light, having a wavelength, incident to said detector at an angle greater than a critical angle, and wherein a refractive index is calculated based on reflected light as measured by said optical sensor.

2. The detector of claim 1 wherein said gap is approximately equal to or less than the wavelength of said light.

3. The detector of claim 1 wherein said first wall and said second wall are translucent.

4. The detector of claim 1 wherein said duct comprises glass.

5. The detector of claim 1 wherein said gap has a cross sectional dimension of between 50 and 1000 nanometers.

6. The detector of claim 1 wherein said duct includes a binding partner for an analyte immobilized on at least a portion of said interior surface of said duct, said binding partner capable of binding to said analyte.

7. The detector of claim 6 wherein said duct has a refractive index greater than a refractive index of said binding partner.

8. The detector of claim 6 wherein said analyte comprises a pathogen, a microorganism, a bacteria, or a virus.

9. The detector of claim 6 wherein said binding partner for said analyte is an antibody or antibody fragment that binds said analyte.

10. The detector of claim 6 wherein said analyte is a ligand specific for a cellular receptor and said binding partner is a cellular receptor.

11. The detector of claim 6 wherein said binding partner is a ligand for a cellular receptor and said analyte is a cellular receptor.

12. The detector of claim 6 wherein said analyte is a metallic ion and said binding partner is a chelator that binds said metallic ion.

* * * * *